United States Patent [19]

Beyersdorf

[11] Patent Number: 5,800,374
[45] Date of Patent: Sep. 1, 1998

[54] REPERFUSION DEVICE

[76] Inventor: Friedhelm Beyersdorf, Am Schlupfloch 35, D-6200 Wiesbaden, Germany

[21] Appl. No.: 197,082

[22] Filed: Aug. 4, 1992

Related U.S. Application Data

[63] Continuation of PCT/EP91/00179, Jan. 31, 1991.

[30] Foreign Application Priority Data

Feb. 6, 1990 [DE] Germany ............... 40 03 425.9

[51] Int. Cl.$^6$ .................. A61M 37/00; A61M 29/00; A61M 31/00
[52] U.S. Cl. .................. 604/4; 604/67; 604/101; 604/102; 128/673
[58] Field of Search .................. 604/4–6, 101, 604/102, 65–67; 128/672, 673

[56] References Cited

U.S. PATENT DOCUMENTS

| 4,610,662 | 9/1986 | Weikl et al. ............... 604/53 |
| 4,648,384 | 3/1987 | Schmukler ............... 128/1 D |
| 4,865,581 | 9/1989 | Lundquist et al. ............... 604/67 |
| 4,976,692 | 12/1990 | Atad ............... 604/101 |
| 5,011,469 | 4/1991 | Buckberg et al. ............... 604/4 |
| 5,014,715 | 5/1991 | Chapolini ............... 128/672 |

FOREIGN PATENT DOCUMENTS

| 0 192 575 | 2/1986 | France ............... A61M 1/10 |
| 2 648 714 | 6/1989 | France ............... A61M 1/36 |
| 0 080 436 | 11/1982 | Germany ............... A61B 17/22 |
| 0 357 338 | 8/1989 | Germany ............... A61M 1/38 |
| 38 20 840 | 11/1989 | Germany . |

Primary Examiner—John G. Weiss
Assistant Examiner—Dennis Ruhl
Attorney, Agent, or Firm—Darby & Darby

[57] ABSTRACT

A reperfusion device draws oxygenated, arterial blood from the patient. This blood is mixed in a mixing container with reperfusion solution. The blood-solution mixture is supplied back to the patient through a catheter and at a place which is upstream from the stenosis being treated. Blood from a blood bank is thus not used. Instead, arterial blood from the patient is used, which is supplied back to the patient immediately after it is prepared with the reperfusion solution. Since the blood leaves the body of the patient for only a short time, damage to the blood is largely avoided. In addition, the pump which supplies the blood-solution mixture to the body of the patient is controlled as a function of the pressure in the blood vessel being treated. The blood pressure is measured for this purpose in the blood vessel, so that very accurate control of the pump is possible.

11 Claims, 2 Drawing Sheets

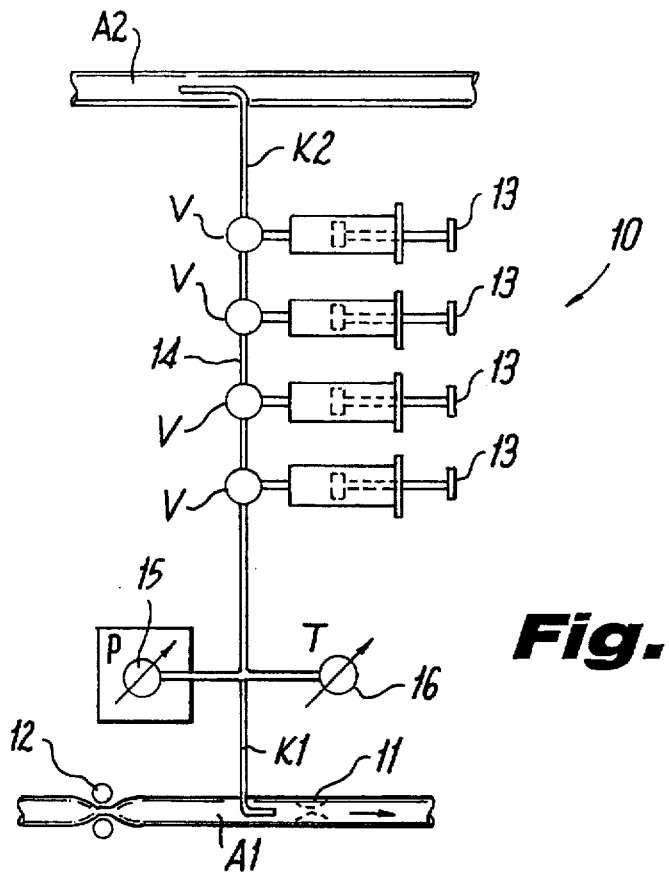
Fig. 2
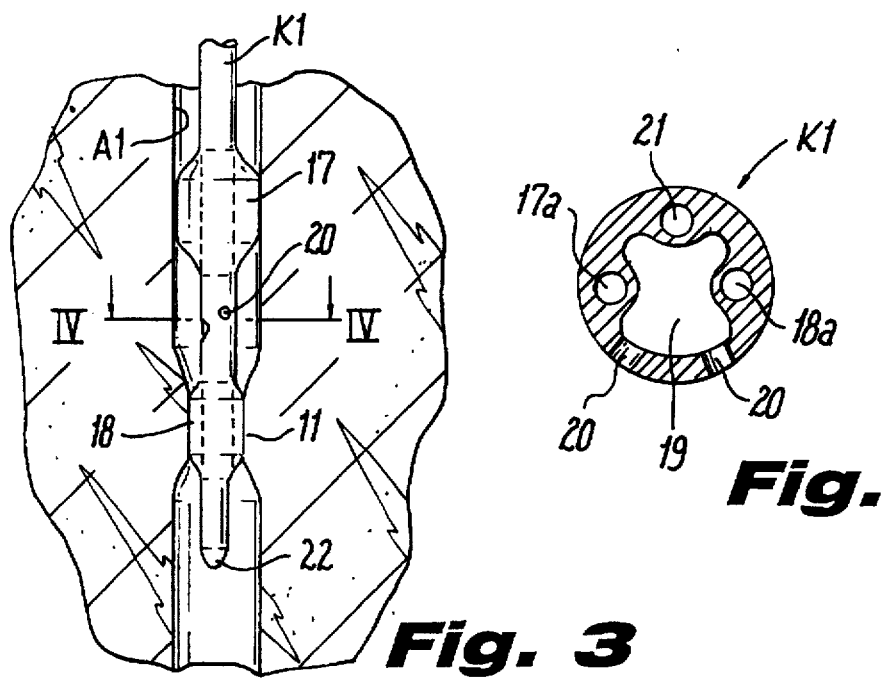
Fig. 3
Fig. 4

REPERFUSION DEVICE

RELATED APPLICATIONS

This is a continuation of International Application PCT/EP91/00179, filed Jan. 31, 1991, claiming priority of German application DE-P 40 03 425.9, filed Feb. 6, 1990.

FIELD OF THE INVENTION

The invention relates to a reperfusion device for the reperfusion of blood vessels.

BACKGROUND OF THE INVENTION

For eliminating vascular occlusion, different methods are known, such as surgical revascularization, the dilation of a stenosed vessel with a balloon catheter or thrombolysis, in which a clot is removed by medicinal drugs that are introduced intra-arterially. Despite successful restoration of the circulatory pathway, the morbidity and mortality of these interventions are relatively high. The main cause of this is reperfusion damage, which occurs when the blood, with full arterial pressure produced by the heart, flows once again through the treated artery. DE 38 20 840 C1 describes an aqueous reperfusion solution for decreasing such reperfusion damage after an acute, peripheral vascular occlusion. This reperfusion solution should be supplied to the patient under a reduced reperfusion pressure, in order to reduce post-ischemic damage.

SUMMARY OF THE INVENTION

It is an object of the invention to deliver a reperfusion solution with simple means under conditions of the greatest safety for the patient.

Pursuant to the invention in the case of the inventive reperfusion device, oxygenated blood is drawn from the patient. This blood, originating from the patient, is mixed in a mixing container with the reperfusion solution. This blood-solution mixture is finally supplied back to the patient through a catheter and at a place which is upstream from the stenosis being treated. Blood from a blood bank is thus not used. Instead, arterial blood from the patient is used, which is supplied back to the patient immediately after it is prepared with the reperfusion solution. Since the blood leaves the body of the patient for only a short time, damage to the blood is largely avoided.

The pump, which supplies the blood-solution mixture to the body of the patient, is preferably controlled as a function of the pressure in the blood vessel being treated. The blood pressure is measured for this purpose in the blood vessel, so that very accurate control of the pump is possible. The blood pressure should be about 50 mm Hg. If it is not possible to measure the arterial blood pressure, for example, when treating the coronary artery, the pump can be controlled in such a manner that it delivers a constant amount per unit time. This amount flowing through the pump is about 50 mL/min. Such an amount flowing into a coronary artery produces a pressure of 50 mm Hg.

The blood-taking set can be connected to the artery to be treated upstream of the stenosis. However, it is advisable to draw the blood from a different artery, because a smaller amount of blood must then be stored in the mixing container.

When carrying out the reperfusion, the blood vessel to be treated advisably is occluded upstream from the stenosis and the blood-solution mixture is passed behind the site of the occlusion into the artery. For this purpose, the catheter has an occlusion balloon, distal of which an outlet is disposed, which is connected with the liquid lumen of the catheter. Aside from the liquid lumen, there is a pressure-measuring lumen in the catheter, which is connected to a pressure gauge.

It should be made certain that air cannot penetrate into the extracorporeal blood flow, so that the danger of an air embolism is avoided. For this purpose, the extracorporeal hose system is constructed without detachable connections. In the case of detachable connectors, the danger exists of opening the blood flow inadvertently.

Moreover, it should be made certain that the mixture supplied to the patient is brought or maintained extracorporeally to body temperature. For this purpose, a controlled heater is provided at the mixing container. Moreover, the extracorporeal blood line, which leads from the mixing container to the patient, is Provided with heat insulation.

The invention makes possible a controlled reperfusion of damaged organs or extremities. The treatment time, during which the blood-solution mixture flows through the blood vessel under a low pressure or with a low flow rate, should be about 30 minutes. After that, the tissue is stabilized to such an extent that the reperfusion can be stopped, so that after the arterial occlusion is eliminated, the blood can flow through the artery with full blood pressure. In principle, it is sufficient to set a particular reperfusion pressure, such as 50 mm Hg, for a particular period of time of several minutes. However, it may also be appropriate to carry out the reperfusion according to a time-dependent pressure profile, during which the reperfusion pressure is increased continuously or discontinuously. This pressure or volume control can be carried out as a function of time by a computer.

BRIEF DESCRIPTION OF THE DRAWINGS

Embodiments of the invention are described in greater detail in the following with reference to the drawings, in which

FIG. 2 shows a representation of a simple embodiment of the device;

FIG. 3 shows a section of catheter introduced into the artery that is to be treated; and FIG. 4 shows a cross section through the catheter along the line IV—IV of FIG. 3.

DESCRIPTION OF THE PREFERRED EMBODIMENTS

Figure 1:
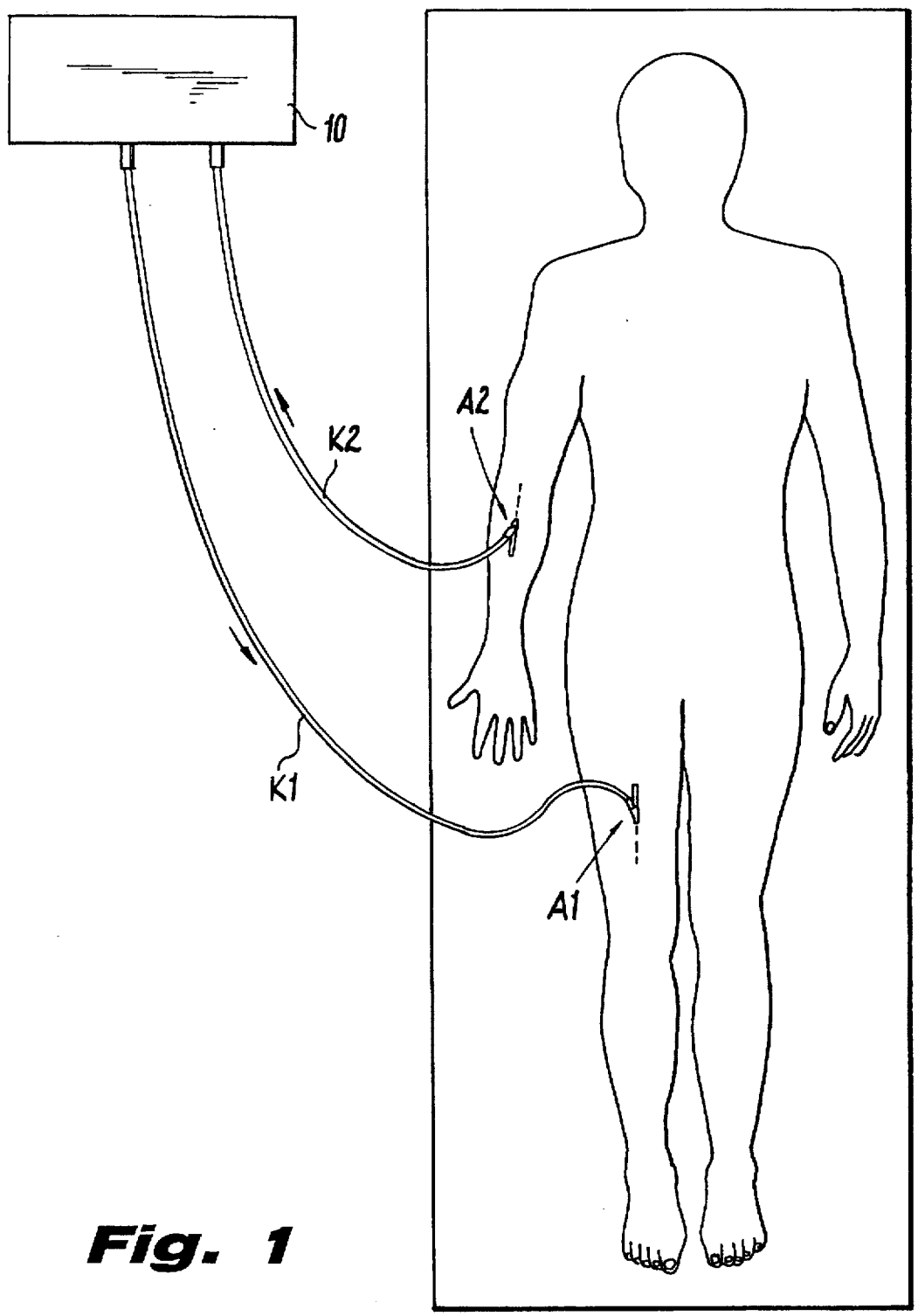
FIG. 1 shows a diagrammatic representation of the connections of a reperfusator to the patient.

According to FIG. 1, a first catheter K1 is placed in the artery A1 that is to be treated. The catheter K1 is supplied by the reperfusator 10 with liquid, which is to be introduced into the artery A1.

From a different (sound) artery A2 of the patient, a further catheter K2 leads to the reperfusator 10. From the artery A2, oxygenated blood flows to the reperfusator 10, where this blood is mixed with a reperfusion solution according to a specified mixing ratio, as described for example, in DE 38 20 840 C1. The mixture is then supplied via the catheter K1 to the artery A1 that is to be treated.

FIG. 2 shows a very simple embodiment of the reperfusator 10, which is suitable for manual operation but can also be operated by a motor. The diseased artery A1 is clamped off upstream from the stenosis with a clamp 12 The stenosis or occlusion is removed and the catheter K1 is placed between the former stenosis 11 and the clamp 12.

Blood is drawn from the healthy artery A2 by means of a single lumen catheter K2 and drawn up in syringes 13, which are partially filled with liquid reperfusion solution, so that, when the syringes 13 are filled completely, the desired blood-solution mixture is obtained. In this case, the syringes 13 form the mixing chambers. Each of these syringes is connected via a valve V to a manifold 14, which is connected with the catheter K1. During the process of filling the syringes 13, the valves V are switched so that liquid cannot infuse yet. At the end of the filling process, the reperfusion can take place, the valves V being switched so that the liquid, when expelled from a syringe 13, can flow from this syringe to the catheter K1 and is kept away from catheter K2.

A pressure gauge 15 and a temperature contracting and measuring device 16 are connected to the manifold 14. These devices produce an alarm signal when the parameter to be measured lies outside of the specified allowable range.

After all the syringes have been drawn up, the valves V are reversed and the contents of the syringes are expressed under the control of the physician, so that a controlled reperfusion takes place by way of the catheter K1. This process is concluded after about 30 minutes. The catheter K1 is removed and the clamp 12 opened.

FIGS. 3 and 4 show an embodiment of the catheter K1. This catheter consists of a flexible tube, which has two balloons 17 and 18, which are mutually spaced apart axially. Balloon 17 is an occlusion balloon for closing off the artery A1 upstream from the stenosis 11 and balloon 18 is a dilation balloon for widening the vessel A1 at the stenosis 11. The liquid lumen 19 of the catheter is provided with outlets 20, which are disposed between the two balloons 17 and 18. A lumen 17a of the catheter K1 serves to supply air to the balloon 17 and a lumen 18a serves to supply air to the balloon 18. A further lumen 21 serves for the measurement of the pressure and, for example, for the connection to the pressure gauge 15 in FIG. 2. The lumen 21 advantageously emerges at the catheter tip 22.

I claim:

1. A reperfusion device for the reperfusion of a blood vessel of a patient, comprising:

a first reperfusion catheter adapted to be introduced into the blood vessel to be reperfused;

blood-taking means for drawing oxygenated, arterial blood from the patient, including a second catheter for withdrawing oxygenated, arterial blood from a different blood vessel than that being reperfused;

a source of reperfusion solution;

a mixing element in fluid communication with said blood-taking means and said source of reperfusion solution, said mixing element forming a blood-solution mixture of the oxygenated, arterial blood drawn from the patient and the reperfusion solution;

means for measuring and controlling temperature coupled to said mixing element; and a delivery device in fluid communication with said first reperfusion catheter and said mixing element, said delivery device driving the blood-solution mixture from said mixing element through said first reperfusion catheter; wherein:

said first reperfusion catheter further includes:

an extracorporeal part leading from said mixing element to the patient, said extracorporeal part being thermally insulated;

a pressure measurement lumen, said pressure measurement lumen emerging within the blood vessel to be reperfused so that said pressure measurement lumen measures the pressure within the blood vessel being treated;

a liquid lumen, the blood-solution mixture being delivered through said liquid lumen to the blood vessel being treated while pressure within the blood vessel being treated is measured with said pressure measurement lumen;

a dilation balloon and an occlusion balloon disposed at a distance from one another; and between the balloons, an outlet in fluid communication with said liquid lumen and through which the blood-solution mixture flows into the blood vessel being treated; and said delivery device is a pumping device and delivers blood-solution mixture as a function of pressure within the blood vessel being treated, as measured by said pressure measurement lumen within the blood vessel being treated, said pumping device further being responsive to the pressure within the blood vessel being treated as measured by said pressure measurement lumen within the blood vessel being treated.

2. A reperfusion device for the reperfusion of a blood vessel of a patient, comprising:

a first reperfusion catheter adapted to be introduced into the blood vessel to be reperfused, said first reperfusion catheter compromising:

a liquid lumen through which a blood-solution mixture flows from said device into the blood vessel being treated;

a pressure measurement lumen emerging within the blood vessel to be reperfused so that said pressure measurement lumen measures the pressure within the blood vessel being treated while blood-solution mixture flows through said liquid lumen;

a dilation balloon and an occlusion balloon disposed at a distance from one another; and between the balloons, an outlet in fluid communication with said liquid lumen through which the blood-solution mixture flows into the blood vessel being treated;

blood-taking means for drawing oxygenated, arterial blood from the patient;

a source of reperfusion solution;

a mixing element in fluid communication with said blood-taking means and said source of reperfusion solution, said mixing element forming a blood-solution mixture of the oxygenated, arterial blood drawn from the patient and the reperfusion solution; and a delivery device in fluid communication with said first reperfusion catheter and said mixing element, wherein said delivery device is a pumping device that drives the blood-solution mixture from said mixing element through said first reperfusion catheter, and is controlled as a function of pressure in the blood vessel being treated, as measured within the blood vessel being treated by said pressure measurement lumen of said first reperfusion catheter, said pumping device being adapted to be responsive to the pressure measured within the blood vessel being treated by said pressure measurement lumen of said first reperfusion catheter.

3. A reperfusion device for the reperfusion of a blood vessel of a patient, comprising:

blood-taking means for drawing oxygenated, arterial blood from the patient;

a source of reperfusion solution;

a mixing element in fluid communication with said blood-taking means and said source of reperfusion solution, said mixing element forming a blood-solution mixture of the oxygenated, arterial blood drawn from the patient and the reperfusion solution;

a first reperfusion catheter adapted to be introduced into the blood vessel to be reperfused, said first reperfusion catheter including a liquid lumen and a pressure measurement lumen, said liquid lumen delivering the blood-solution mixture to the blood vessel being treated through an outlet defined in said first reperfusion catheter, and said pressure measurement lumen emerging within the blood vessel being treated so that said pressure measurement lumen measures the pressure within the blood vessel being treated while blood-solution is steadily delivered through said liquid lumen; and a delivery device in fluid communication with said first reperfusion catheter and said mixing element, wherein said delivery device drives the blood-solution mixture from said mixing element through said liquid lumen of said first reperfusion catheter as a function of and in response to pressure in the blood vessel being treated, as measured by said pressure measurement lumen of said first reperfusion catheter.

4. The reperfusion device of claim 3, wherein said blood-taking means includes a second catheter for withdrawing oxygenated, arterial blood from a healthy artery, different from the blood vessel being reperfused.

5. The reperfusion device of claim 3, further comprising means for measuring and controlling the temperature of said blood-solution mixture coupled to said mixing element.

6. The reperfusion device of claim 3, wherein an extra-corporeal part of said first reperfusion catheter leading from said mixing element to the patient is thermally insulated.

7. The reperfusion device of claim 3, wherein said delivery device includes a pump.

8. The reperfusion device of claim 3, wherein said first reperfusion catheter further comprises:

a dilation balloon and an occlusion balloon disposed at a distance from one another; and an air supply lumen defined within said first reperfusion catheter;

wherein the outlet in fluid communication with said liquid lumen of said first reperfusion catheter is defined between said balloons.

9. The reperfusion device of claim 8, wherein said blood-taking means includes a second catheter for withdrawing oxygenated, arterial blood from a health artery different from the blood vessel being reperfused.

10. The reperfusion device of claim 8, further comprising means for measuring and controlling the temperature of said blood-solution mixture coupled to said mixing element.

11. The reperfusion device of claim 8, wherein an extra-corporeal part of said first reperfusion catheter leading from said mixing element to the patient is thermally insulated.

* * * * *